(12) United States Patent
Crespy et al.

(10) Patent No.: US 8,932,579 B2
(45) Date of Patent: Jan. 13, 2015

(54) BIOLOGICAL EFFECTS OF COMPOSITIONS COMPRISING ROSMARINIC ACID

(75) Inventors: Vanessa Crespy, Vevey (CH); Isabelle Castiel, Nice (FR); Rachid Bel-Rhlid, Savigny (CH); Nicolas Page, Lausanne (CH); Thomas Raab, Grandvaux (CH)

(73) Assignees: Nestec S.A., Vevey (CH); L'Oreal, Paris (FR)

( * ) Notice: Subject to any disclaimer, the term of this patent is extended or adjusted under 35 U.S.C. 154(b) by 1248 days.

(21) Appl. No.: 12/513,631

(22) PCT Filed: Nov. 6, 2007

(86) PCT No.: PCT/EP2007/009602
§ 371 (c)(1),
(2), (4) Date: Dec. 15, 2009

(87) PCT Pub. No.: WO2008/055651
PCT Pub. Date: May 15, 2008

(65) Prior Publication Data
US 2010/0129324 A1 May 27, 2010

Related U.S. Application Data

(60) Provisional application No. 60/869,615, filed on Dec. 12, 2006.

(30) Foreign Application Priority Data

Nov. 6, 2006 (EP) .................................. 06023060

(51) Int. Cl.
| | | |
|---|---|---|
| A61K 35/74 | (2006.01) | |
| A23L 1/28 | (2006.01) | |
| A23L 1/30 | (2006.01) | |
| A61K 31/216 | (2006.01) | |
| A61K 36/53 | (2006.01) | |
| A61K 38/46 | (2006.01) | |

(52) U.S. Cl.
CPC .............. *A61K 35/747* (2013.01); *A23L 1/28* (2013.01); *A23L 1/30* (2013.01); *A23L 1/3002* (2013.01); *A23L 1/3014* (2013.01); *A23L 1/3016* (2013.01); *A61K 31/216* (2013.01); *A61K 35/745* (2013.01); *A61K 36/53* (2013.01); *A61K 38/465* (2013.01); *A23V 2002/00* (2013.01)
USPC ........................................ 424/93.4

(58) Field of Classification Search
USPC .................................. 424/70, 93.4
See application file for complete search history.

(56) References Cited

U.S. PATENT DOCUMENTS

| | | | |
|---|---|---|---|
| 5,603,930 A | 2/1997 | Brassart et al. | |
| 5,932,234 A | * 8/1999 | Simon et al. | ................... 424/401 |
| 2003/0049231 A1 | * 3/2003 | Baur et al. | ................... 424/93.4 |
| 2004/0009244 A1 | 1/2004 | Kim et al. | ...................... 424/729 |
| 2004/0037901 A1 | 2/2004 | Breton et al. | .................. 424/745 |
| 2005/0037094 A1 | 2/2005 | Yan et al. | ....................... 424/728 |
| 2006/0018867 A1 | * 1/2006 | Kawasaki et al. | ......... 424/70.122 |
| 2006/0172402 A1 | * 8/2006 | Havkin-Krenkel et al. | .. 435/147 |
| 2006/0269508 A1 | * 11/2006 | Trejo | ............................... 424/74 |

FOREIGN PATENT DOCUMENTS

| | | |
|---|---|---|
| WO | WO 96/39859 A1 | 12/1996 |
| WO | WO0182715 A2 | 11/2001 |
| WO | WO 2004/058282 A2 | 7/2004 |

OTHER PUBLICATIONS

Derwent, Derwent Abstract of EP1269857, 2003, Derwent Accession No. 2001-618111, pp. 1-3.*
Konishi et al. Transepithelial transport of rosmarinic acid in intestinal CACO2 cell monolayers. 2005;69(3):583-591.*
Reuter G. The *Lactobacillus* and *Bifidobacterium* microflora of the human intestine: Composition and succession. 2001;2(2):43-53.*
Konishi et al. Transepithelial transport of rosmarinic acid in intestinal caco-2 cell monolayers. Biosci. Biotechnol. Biochem. 2005;69(3):583-591.*
Lahtinen et al. Intrinsic properties of so-called dormant probiotic bacteria, determined by flow cytometric viability assays. Applied and Environmental Microbiology. 2006;72(7):5132-5134.*
RAD. Potential of origanox in cosmetics applications. Technical bulletin. 2000.*
Rechner et al. Colonic metabolism of dietary polyphenols: influence of structure on microbial fermentation products. Free Radical Biology & Medicine. 2004;36(2):212-225.*
Pridmore et al. The genome sequence of the probiotic intestinal bacterium *Lactobacillus johnsonii* NCC 533. PNAS. 2004;101(8):2512-2517.*
Luis et al. Seasonal variations of rosmarinic and carnosic acids in rosemary extracts. Analysis of their in vitro antiradical activity. Spanish Journal of Agricultural Research. 2005;3(1)106-112.*

(Continued)

*Primary Examiner* — Ruth Davis
*Assistant Examiner* — Lynn Y Fan
(74) *Attorney, Agent, or Firm* — Winston & Strawn LLP (57) ABSTRACT

The present invention relates to compositions of rosmarinic acid or its derivatives and to the use of a hydrolytic enzyme or of microorganism containing or producing hydrolytic enzymes in these compositions. The invention also pertains to methods for improving the biological effects of the rosemary extracts and for administering such compositions to a human or animal subject for improving the skin, coat, hair or health of the subject.

5 Claims, 4 Drawing Sheets

(56) References Cited

OTHER PUBLICATIONS

European Search Report Application No. EP06023060 dated Mar. 21, 2007.
Rechner Andreas R. et al, XP002425757, "The Metabolic Fate of Dietary Polyphenols in Humans.", Free Radical Biology & Medicine, vol. 33, No. 2, pp. 220-235 (2002).
Konishi Yutaka et al., XP002425758, "Transepithelial Transport of Rosmarinic Acid in Intestinal Caco-2 Cell Monolayers.", Bioscience, Biotechnology and Biochemistry, vol. 69, No. 3, pp. 583-591, (2005).
Baba S. et al., XP019383030, "Absorption. Metabolism Degradation and Urinary Excretion of Rosmarinic Acid After Intake of *Perilla frutescens* Extract in Humans" European Journal of Nutrition, vol. 44, No. 1, pp. 1-9 (2005).
International Search Report PCT/EP2007/009602 Dated Jan. 15, 2008.
Konishi et al. *Pharmacokinetic Study of Caffeic and Rosmarinic Acids in Rats After Oral Administration*, pp. 4740-4746, Journal of Agricultural and Food Chemistry, vol. 53, No. 12 (Jun. 15, 2005) (XP002425756).
Donaghy et al. *Detection of Ferulic Acid Esterase Production by Bacillus Spp. and Lactobacilli*, pp. 257-260, Applied Microbiology and Biotechnology, Springer Verlag, vol. 50, (1998) (XP002356885).
Al-Sereiti et al. *Pharmacology of Rosemary(Rosmarinus officinalis Linn.) and Its Therapeutic Potentials*, pp. 124-130, Indian Journal of Experimental Biology, vol. 37 (Feb. 1999) (XP002909319).
Lu et al. *Polyphenolics of Salvia—A Review*, Phytochemistry Pergamon Press, GB, pp. 117-140, vol. 59, No. 2, (Jan. 2002) (XP004332841).
Wojciechowski et al. *Analysis of the Components of Lycopus europaeus L. in Body Fluids During Metabolism Studies; Comparison of Capillary Electrophoresis and High Performance Liquid Chromatography*, pp. 261-270, Journal of Chromatography A, Elsevier, vol. 717, No. 1 (Nov. 24, 1995) (XP004038549).
Psotova et al. *Photoprotective Properties of Prunella vulgaris and Rosmarinic Acid on Human Keratinocytes*, pp. 167-174, Journal of Photochemistry & Photobiology B: Biology, Elsevier Science S.A., Basel, vol. 84, No. 3 (Sep. 1, 2006) (XP005600792).
Database WPI Week 200419, Derwent Publications Ltd., London, GB AN 2004-199501, KR 2003 082 764 A (Sk Chem Co. Ltd) (Oct. 23, 2003) (XP002425800).
Gobbetti et al. *Esterolytic and Lipolytic Activities of Mesophilic and Thermophilic Lactobacilli*, Online Database BIOSIS, Biosciences Information Service, Philadelphia, PA (1996), Database Accession No. PREV199699150347 and Italian Journal of Food Science, vol. 8, No. 2, (1996) pp. 127-135 (XP002425763).
Del Bano et al., "Radioprotective Antimutagenic Effects of Rosemary Phenolics against Chromosomal Damage induced in Human Lymphocytes by Gamma-Rays"; Journal of Agricultural and Food Chemistry, 2006, vol. 54, p. 2064-2068.
M. Petersen and M.S.J. Simmonds, "Rosmarinic Acid"; Phytochemistry; 2003, vol. 62, p. 121-125.
Swanson L., What You Need to Know About Probiotic Strains: *Lactobacillus*, Probiotics 101 2013, p. 1-3.
Petersen et al., Evolution of Rosmarinic Acid Biosynthesis, Phytochemistry. 2009, vol. 70, p. 1663-1679.
Bei-Rhlid et al., Hydrolysis of Rosmarinic Acid From Rosemary Extract With Esterases and *Lactobacillus johnsonii* In Vitro and in a Gastrointestinal Model, Journal of Agricultural and Food Chemistry, 2009, vol. 57, p. 7700-7705.

* cited by examiner

BIOLOGICAL EFFECTS OF COMPOSITIONS COMPRISING ROSMARINIC ACID

This application is a 371 filing of International Patent Application PCT/EP2007/009602, filed Nov. 6, 2007, which claims the benefit of European Patent Application No. EP 06023060.4, filed Nov. 6, 2006 and U.S. Provisional Patent Application No. 60/869,615, filed Dec. 12, 2006.

FIELD OF THE INVENTION

The present invention relates to compositions comprising rosmarinic acid or extracts containing rosmarinic acid and to the use of a hydrolytic enzyme or of microorganisms containing or capable of producing hydrolytic enzymes in these compositions. The invention also pertains to methods for improving the biological effects of compositions containing rosmarinic acid and its derivatives.

BACKGROUND ART

Rosmarinic acid is a polyphenol found in a number of natural sources including rosemary, oregano, marjoram, thyme, peppermint, comfrey, parsley, balm, sage, hyssop, basil, lavender etc. These plants have been reported as herbal remedies with antioxidant, anti-inflammatory, anticarcinogenic, and hepatoprotective properties. These biological effects have been related to the presence of polyphenols, notably rosmarinic acid, flavones, and flavanols which were identified in rosemary leaves, for instance.

There is no way described in the art as to how to improve the biological effects of compositions comprising rosmarinic acid or plant extracts comprising said rosmarinic acid.

OBJECT OF THE INVENTION

There thus remains a need to improve the biological effects of compositions comprising rosmarinic acid or plant extracts comprising said rosmarinic acid and derivatives thereof.

SUMMARY OF THE INVENTION

Accordingly, this object is solved by the features of the independent claims. The dependent claims further develop the central idea of the invention.

Thus, in a first aspect, the present invention relates to a composition comprising rosmarinic acid and/or derivatives thereof in combination with a hydrolytic enzyme and/or with a microorganism containing or producing said enzyme.

In a second aspect, the invention relates to a composition comprising rosmarinic acid and/or derivatives thereof in combination with a hydrolysis product thereof.

A composition according to any of claims 1 to 15 for use in improving or preventing damages to the skin is also part of the present invention.

Further, the invention encompasses the cosmetic use of a composition according to any of claims 1 to 15.

In another aspect, the invention pertains to the use of a hydrolytic enzyme or a microorganism containing or producing said enzyme for hydrolysing rosmarinic acid.

The use of a hydrolytic enzyme or a microorganism containing or producing said enzyme in a composition comprising rosmarinic acid and/or its derivatives for improving the biological effect of said composition falls under a further aspect of the invention.

Further, the invention also provides a method of preparing a composition comprising rosmarinic acid and/or derivatives thereof having an increased biological effect comprising the steps of:
  a. Providing rosmarinic acid and/or derivatives thereof,
  b. Providing a hydrolytic enzyme or a microorganism containing or producing said enzyme, and
  c. Mixing said rosmarinic acid and/or derivatives thereof and hydrolytic enzyme or microorganism containing or producing said enzyme with further ingredients to produce said composition, such that hydrolysis of rosmarinic acid occurs in the composition or in vivo.

Finally, a method is provided for improving the health of a subject comprising the step of administering a composition according to any of claims 1 to 15.

FIGURES

The present invention is further described hereinafter with reference to some of its embodiments shown in the accompanying drawings wherein.

DETAILED DESCRIPTION OF THE INVENTION

The present invention relates to compositions comprising rosmarinic acid and derivatives thereof. The compositions may be "food compositions" or "topical compositions". By "food compositions" is meant any consumable product which can be used for nutritional, pharmaceutical and/or cosmetic purposes. By "topical compositions" is meant any composition that can be applied to the skin, coat, nails or hair of a subject for pharmaceutical and/or cosmetic purposes. Preferably, the compositions are food compositions.

Rosmarinic acid (FIG. 1) and its derivatives are commonly found in plants such as rosemary, oregano, marjoram, thyme, peppermint, comfrey, parsley, balm, sage, hyssop, basil, lavender, perilla etc.

By "derivatives" of rosmarinic acid is meant any compound comprising at least a rosmarinic acid moiety. These include oligomers, polymers, glucosides of rosmarinic acid etc. Rosmarinic acid and its derivatives may be provided as pure compounds or by various herbs such as perilla (*Perilla*

*frutescens* L.), sage (*Salvia officinalis* L.), mint (*Mentha arvense* L.), basil (*Ocimum basilicum* L.), thyme (*Thymus vulgaris* L.), Chinese bitter-sweet (*Celastrus hindsii*) etc. Preferably it is provided by rosemary (*Rosmarinus officinalis* L.).

Furthermore, extraction of plants containing a rosmarinic acid source may be carried out using methods known in the art. Indeed, the composition of the present invention preferably comprises plant extracts comprising rosmarinic acid and/or its derivatives. Preferably, the extracts are present in the composition in an amount ranging from 0.01 g to 20 g on a dry matter basis.

The present invention thus provides a composition comprising rosmarinic acid and/or derivatives thereof in combination with a hydrolytic enzyme (e.g. esterase) or a microorganism containing or producing a hydrolytic enzyme capable of hydrolysing rosmarinic acid or its derivatives.

Due to the hydrolytic effect of the enzyme on rosmarinic acid and/or on its derivatives, the composition may further comprise the hydrolysis products of rosmarinic acid and/or its derivatives with said enzyme. These may include caffeic acid, 3,4-dihydroxy phenyllacetic acid etc. and mixtures thereof.

The compositions of the present invention may be dry, moist, or semi-moist compositions. By "dry" are meant compositions having a water activity below 0.6. By "semi-moist" are meant compositions having a water activity between 0.6 and 0.9 and by "moist" are meant compositions having a water activity above 0.9.

The compositions may comprise suitable food or pharmaceutical carriers. These include milk, yogurt, cheese, fermented milk, milk-based fermented products, ice creams, fermented cereal-based products, milk-based powders, formulae for children and infants, foods for animal, in particular pets, tablets or lozenges, liquid bacterial suspensions, oral supplements in dry form and oral supplements in liquid form.

Thus, the composition may be a food composition in the form of complete nutritional foods, drinks, mineral waters, soups, food supplements and replacement foods, solutions, sprays, powders, tablets, capsules, nutritional bars, liquid bacterial suspensions, confectionery, milk-based or fermented milk-based products, yogurts, milk-based powders, enteral nutrition products, compositions for children and/or infants, cereal-based products or fermented cereal-based products, soy-based products, ice creams, chocolate, coffee, "culinary" products such as mayonnaise, tomato puree or salad dressings, pet food etc. Thus, the composition may also be intended for animals.

For ingestion, many embodiments of oral compositions and in particular of food supplements are possible. They are formulated by means of the usual methods for producing sugar-coated tablets, gelatine capsules, gels, emulsions, tablets, capsules or solutions. In particular, the composition comprising rosmarinic acid and/or a derivative thereof in combination with a hydrolytic enzyme or with a microorganism containing or producing said enzyme may be incorporated into any other forms of food supplements or of enriched foods, for example food bars, or compacted or non-compacted powders. The powders can be diluted with water, in a fizzy drink, dairy products or soy-derived products or can be incorporated into food bars.

Alternatively, the composition may be a topical composition in the form of aqueous, aqueous-alcoholic or oily solutions, of dispersions of the solution type or dispersions of the lotion or serum type, of emulsions that have a liquid or semi-liquid consistency of the milk type, obtained by dispersion of a fatty phase in an aqueous phase (O/W) or vice-versa (W/O), or of suspensions or emulsion that have a soft, semi-solid or solid consistency of the cream, aqueous gel or anhydrous gel type or else of microemulsions, of microcapsules, or microparticles or of vesicular dispersions of ionic and/or non-ionic type.

The compositions of the invention may comprise the usual excipients and constituents, e.g. fatty and/or aqueous constituents, humectifying agents, thickeners, preserving agents, texturing, flavouring and/or coating agents, antioxidants, dyes that are usual in the food and/or topical domain.

Preferably, the hydrolytic enzyme present in the composition is an esterase.

The underlying principle of the present invention is that certain hydrolytic enzymes are capable of cleaving rosmarinic acid (FIG. 1) into caffeic acid (FIG. 2) and 3,4-dihydroxy phenyllacetic acid (FIG. 3) which are more readily bioavailable than rosmarinic acid. Thus, the bioefficacy of compositions comprising rosmarinic acid or plant extracts comprising rosmarinic acid is improved.

By providing a composition comprising said hydrolytic enzyme, the present invention allows the process of converting rosmarinic acid into caffeic acid and 3,4-dihydroxy phenyllacetic acid described above to occur either in the food matrix itself, in the product for topical application itself, or at an early stage of the digestion process in vivo or upon topical application, thus increasing the bioefficacy of compositions comprising rosmarinic acid and/or its derivatives.

Thus, the compositions of the invention containing rosmarinic acid and/or its derivatives have improved biological effects.

Alternatively or in addition, the composition of the present invention may comprise a microorganism containing or producing such a hydrolytic enzyme.

Figure 2:
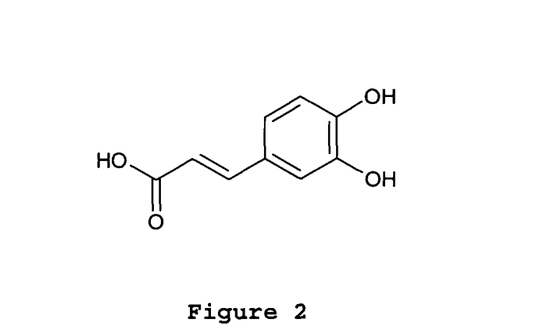
FIG. 2 depicts the molecular structure of caffeic acid.
Figure 3:
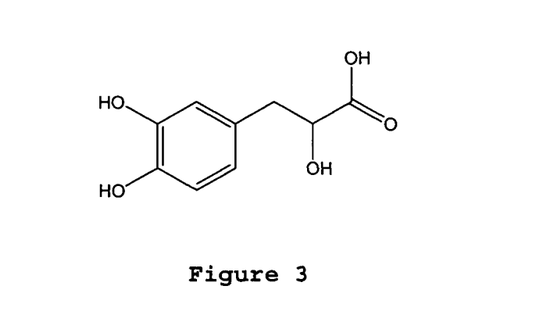
FIG. 3 depicts the molecular structure of 3,4-dihydroxy phenyllacetic acid.

The amount of enzyme or microorganism present in the composition of the invention is such that at least 10%, preferably at least 30%, more preferably at least 50% of rosmarinic acid (FIG. 1) can be hydrolysed into caffeic acid (FIG. 2) and 3,4-dihydroxy phenyllacetic acid (FIG. 3). This can be easily determined by the skilled person by methods known in the art.

Depending on the application, the hydrolytic enzyme may be present in the composition in an amount ranging from 0.01 to 1000 U/g.

When the microorganism is used in the composition, it is preferably present in an amount ranging from $1\times10^3$ to $1\times10^{12}$ cfu/g.

The microorganism used in the composition of the invention may be selected from bacteria, yeasts or fungi. Preferably, the microorganism is a probiotic microorganism. More preferably, it is selected from *Lactobacillus johnsonii* (CNCM I-1225), *Bifidobacterium longum* (ATCC BAA-999), *Bifidobacterium lactis* (CNCM I-3446) or mixtures thereof.

Under another aspect of the invention, a composition comprising rosmarinic acid or plant extracts comprising rosmarinic acid and/or derivatives thereof in combination with a hydrolysis product thereof is provided. Preferably, the hydrolysis product is obtainable by enzymatic cleavage of rosmarinic acid and/or derivatives thereof. Such hydrolysis product may be selected from caffeic acid, 3,4-dihydroxy phenyllacetic acid etc. and mixtures thereof.

Figure 8:
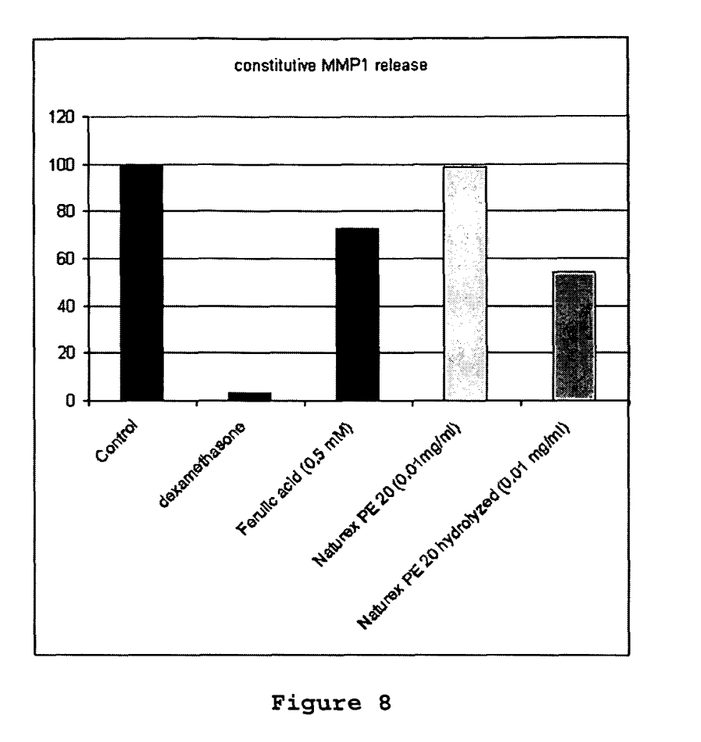
FIG. 8 is a graph showing the improved biological effect of an extract containing rosmarinic acid after hydrolysis (Naturex PE20 hydrolysed) compared with an extract comprising rosmarinic acid (Naturex PE20).

The compositions of the invention are particularly useful in improving or preventing damages to the skin. Indeed, they have been found to be particularly useful in inhibiting the expression of matrix metalloproteinase. Preferably, the matrix metalloproteinase is of type 1. FIG. 8 shows the effect of hydrolysis on an extract comprising rosmarinic acid in the constitutive MMP1 release. It can be seen that compared to a control, to ferulic acid, and to an extract comprising rosmarinic acid (not hydrolysed), at least partially hydrolysed rosmarinic acid has a considerably effect on the constitutive MMP1 release which makes it particularly useful in improving and/or preventing damages to the skin.

According to an embodiment, the composition of the invention may be used cosmetically. In this embodiment, the compositions may be designed for oral consumption or for topical applications.

By "cosmetic use" is meant a non-therapeutic use which may improve the aesthetic aspect or comfort of the skin, coat and/or hair of humans or pets.

In this context, the cosmetic use may include preventing damages to, and/or improving the skin, coat and/or hair of humans or pets. Such damages include in particular actinic and ageing damages of the skin such as dryness, irregular pigmentation (notably freckling, lentigines, guttate hypomelanosis and persistent hyperpigmentation), wrinkling (notably fine surface lines and deep furrows), stellate pseudoscars, elastosis, inelasticity, telangiectasia, venous lakes, comedones, sebaceous hyperplasia, acrochordon and seborrhea keratosis.

The cosmetic use may also have particular benefits on hair and coat, such as an improved hair or coat density, fibre diameter, colour, oiliness, glossiness, sebum production and may help to prevent hair or coat loss.

When used cosmetically, the composition of the invention may assume any form of food composition described above. Preferably, it is in the form of dietary supplements, which may be in liquid or dry form, such as solutions, sprays, tablets, capsules, gelatine capsules, lozenges, powders, gels, emulsions etc. More preferably it is in the form of a capsule.

Alternatively, the composition may assume the form of a topical composition which can be in the form of aqueous, aqueous-alcoholic or oily solutions, of dispersions of the solution type or dispersions of the lotion or serum type, of emulsions that have a liquid or semi-liquid consistency of the milk type, obtained by dispersion of a fatty phase in an aqueous phase (O/W) or vice-versa (W/O), or of suspensions or emulsion that have a soft, semi-solid or solid consistency of the cream, aqueous gel or anhydrous gel type or else of microemulsions, of microcapsules, or microparticles or of vesicular dispersions of ionic and/or non-ionic type.

These compositions are prepared according to usual methods known to the skilled person. In a preferred embodiment, these topical compositions are designed such that the enzyme and/or microorganism interact with the rosmarinic acid only upon topical application.

Compositions for topical applications can in particular constitute cleansing, protective, treatment or care creams for the face, for the hands, for the feet, for the major anatomical folds or for the body (for example day creams, night creams, makeup-removing creams, foundation creams, sun creams), makeup products such as fluid foundations, makeup-removal milks, protective or care milks for the body, aftersun milks, skincare lotions, gels or foams, such as cleansing or disinfecting lotions, sun lotions, artificial tanning lotions, bath compositions, deodorant compositions containing a bactericidal agent, aftershave gels or lotions, depilatory creams, or compositions for insect bites, soaps, cleansing cakes, creams, gels, emulsions or mousses, aerosol compositions for hair etc.

Figure 1:
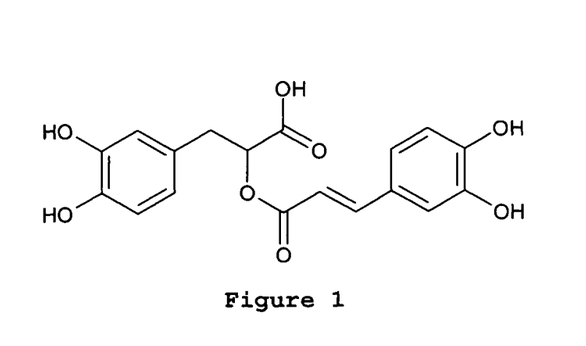
FIG. 1 depicts the molecular structure of rosmarinic acid.

In another aspect, the present invention relates to the use of hydrolytic enzyme or a microorganism containing or producing a hydrolytic enzyme for hydrolysing rosmarinic acid (FIG. 1). Referring to FIGS. 4 to 7, the hydrolysis of rosmarinic acid into caffeic acid (FIG. 2) and 3,4-dihydroxy phenyllacetic acid (FIG. 3) may depend on the amount of enzyme used, the pH and the temperature at which the hydrolysis is carried out and the amount of rosmarinic acid present.

The use of a hydrolytic enzyme or a microorganism containing or producing said hydrolytic enzyme in a composition comprising rosmarinic acid and/or its derivatives for improving the bioefficacy of said composition is thus provided by the present invention.

When a microorganism is used for this purpose, it is preferably selected from bacteria, yeasts or fungi. More preferably it is a probiotic microorganism. Most preferably, it is selected from *Lactobacillus johnsonii* (CNCM I-1225), *Bifidobacterium longum* (ATCC BAA-999), *Bifidobacterium lactis* (CNCM I-3446) or mixtures thereof.

According to another embodiment of the present invention, a method of preparing a composition comprising rosmarinic acid and/or its derivatives having an increased bioefficacy is given.

The method comprises the first step of providing rosmarinic acid and/or its derivatives. This may be provided by various herbs such as rosemary, oregano, marjoram, thyme, perilla, peppermint, comfrey, parsley, balm, sage, hyssop, basil, lavender etc. or mixtures thereof, or by extraction of natural sources.

Preferably, rosmarinic acid is provided in an amount ranging from 0.01 mg to log on a dry matter basis.

Secondly, a hydrolytic enzyme or a microorganism containing or producing said hydrolytic enzyme is provided.

When the enzyme is used as such, it is preferably provided in an amount ranging from 0.01-1000 U/g.

If the microorganism is used, it is preferably provided in an amount ranging from $1\times10^3$ to $1\times10^{12}$ cfu/g. The microorganism may be selected from bacteria, yeasts or fungi. According to a preferred embodiment, the microorganism is a probiotic. More preferably, it is selected from *Lactobacillus johnsonii* (CNCM I-1225), *Bifidobacterium longum* (ATCC BAA-999), *Bifidobacterium lactis* (CNCM I-3446) or mixtures thereof.

The third step of the method then consists in mixing the rosmarinic acid and/or derivatives thereof and the hydrolytic enzyme and/or microorganism containing or producing said enzyme with further ingredients to produce said composition, such that hydrolysis of rosmarinic acid occurs in the composition or in vivo.

The process of converting rosmarinic acid into caffeic acid and 3,4-dihydroxy phenyllacetic acid described above may thus occur either in the food matrix itself, in the product for topical application itself, or at an early stage of the digestion process in vivo or upon topical application thus increasing the bioefficacy of said compositions comprising rosmarinic acid and/or its derivatives.

Further ingredients may include any ingredients used in the manufacture of food products, of topical compositions and functional ingredients. These include carbohydrates, proteins, lipids, fibres, vitamins, prebiotics, minerals, plant extracts etc.

The resulting composition may be in any form such as those compositions described above.

The present invention further encompasses a method for improving the health of a subject, comprising the step of administering a composition according to any of claims 1 to 15. Administration may be topical or oral.

The composition of the invention indeed may act as an anti-oxidant, as an anti-inflammatory and anti-hypertensive. Further, it has positive effects in the prevention or treatment of cardiovascular and cerebrovascular diseases, in the prevention of type 2 diabetes, and in brain degenerative diseases.

Furthermore, the compositions according to the present invention may be administered for treating and/or preventing damages of the skin which are, for example, produced by a stress situation e.g. by means of a chemical, biological or a physical stress, e.g. by exposure to oxidants or carcinogens, exposure to bacteria, viruses, fungi, lipids derived from surrounding cells and/or microbes, or exposure to UV-irradiation.

These damages further comprise actinic keratoses, purpura, cherry angiodema, basal cell carcinoma and squamous cell carcinoma, skin burning and/or blistering, epidermal hyperplasia, inflammation, immune suppression, and cancer, e.g. non-melanoma and melanoma skin cancers.

The effect of the compositions according to the present invention, on skin of humans or pets, can be measured by using conventional methods including minimal erythemal dose (MED), colorimetry, transepidermal water loss, DNA repair, measure of interleukins and proteoglycans production, or collagenase activity, barrier function or cell renewal. A composition according to the invention is thus useful in improving and preventing damages to the skin.

It will be understood that the concept of the present invention may likewise be applied as an adjuvant therapy assisting in presently used medications. Since the compositions of the present invention may easily be orally administered with food material, special clinical food may be administered containing a high amount of the objective substances.

The present invention is further illustrated by means of the non-limiting examples described below.

EXAMPLES

Example 1

Cosmetic for Oral Administration

A composition in the form of a hard capsule has the following formulation:

| Compound | mg per capsule |
| --- | --- |
| Rosemary extract | 500 |
| *Lactobacillus johnsonii* | $5 \times 10^8$ cfu |
| Excipient for the core | |
| Microcrystalline Cellulose | 70 |
| Encompress ™ | 60 |
| Magnesium stearate | 3 |
| Anhydrous colloidal Silica | 1 |
| Coating agent | |
| Gum-lac | 5 |
| Talc | 61 |
| Sucrose | 250 |
| polyvidone | 6 |
| titanium dioxide | 0.3 |
| colouring agent | 5 |

The composition can be administered to the individual in an amount of 2 to 3 capsules daily.

Example 2

A food recipe was prepared by mixing rosemary extract (or rosmarinic acid) with *Lactobacillus johnsonii* (La1, CNCM I-1225) in the proportion of $1 \times 10^5$ to $1 \times 10^{12}$ cfu of bacteria to 1 g to 10 g of the rosemary extract (or rosmarinic acid). The resulting mixture was added or blended with any suitable carrier, for example a fermented milk, a yoghurt, a fresh cheese, a renneted milk, a confectionery bar, breakfast cereal flakes or bars, a drink, milk powder, soy-based product, non-milk fermented product or a nutritional supplement for clinical nutrition.

Example 3

Cleavage of Rosmarinic Acid by Enzymes

Influence of Enzyme Amount

Figure 4:
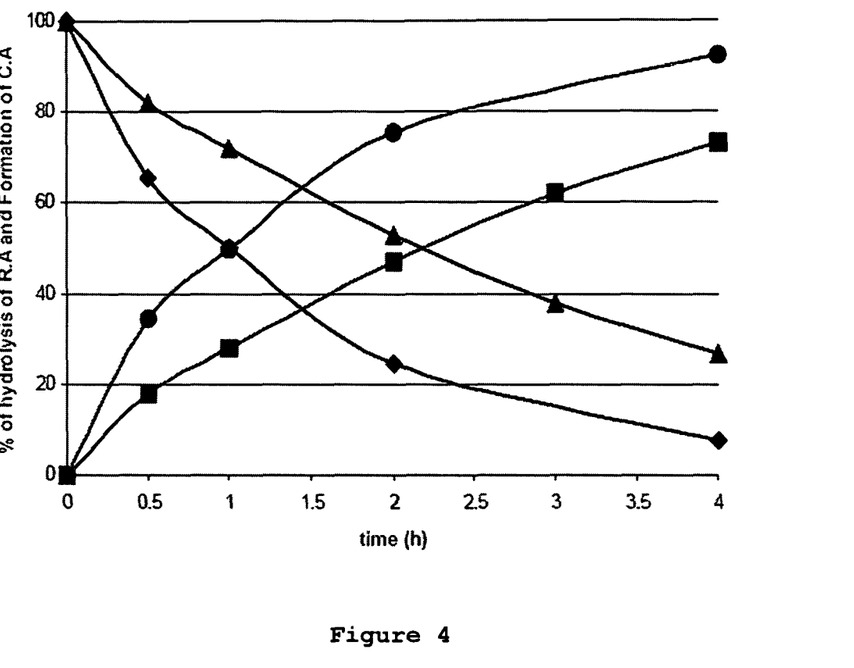
FIG. 4 is a graph showing the influence of chlorogenate esterase enzyme amount on the hydrolysis of rosmarinic acid ((▲) 0.01 U/mg, (♦) 0.02 U/mg) and on formation of caffeic acid ((□) 0.01 U/mg, (•) 0.02 U/mg)

Trials were performed in phosphate buffer (50 mM, pH 6.6) at 40° C. using different amounts of enzyme (0.01 U, 0.02 U and 1 U enzyme/mg rosmarinic acid). As shown in FIG. 4, the reaction rate was proportional to the enzyme amount and when chlorogenate esterase was used at 1 U/mg of substrate, rosmarinic acid was completely transformed into caffeic acid and 3,4-dihydroxy phenyllacetic acid after only 30 min reaction time (data not shown).

Influence of pH

Figure 5:
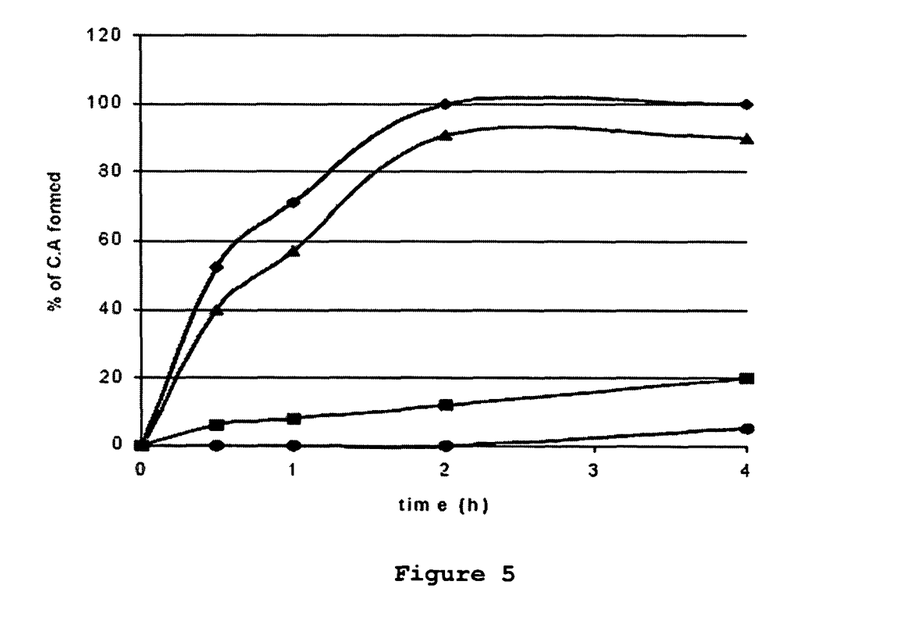
FIG. 5 is a graph showing the influence of pH on the formation of caffeic acid from rosmarinic acid using chlorogenate esterase enzyme at pH 5.0 (•), pH 6.0 (□), pH 7.0 (▲), and pH 8.0 (♦)

The influence of pH on the enzymatic hydrolysis (0.02 U/mg) of rosmarinic acid was studied. FIG. 5 shows the generation of caffeic acid at the pH values of 5.0, 6.0, 7.0 and 8.0. At pH 8.0, rosmarinic acid was completely transformed after 2 h reaction time while the reaction rate was very low at pH 6.0 and no hydrolysis was observed at pH 5.0.

Influence of Temperature

Figure 6:
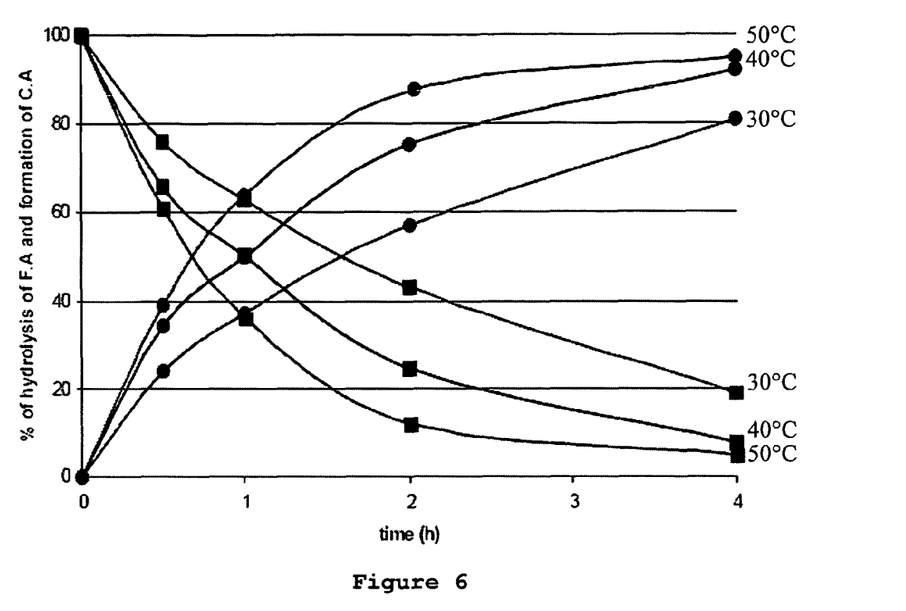
FIG. 6 is a graph showing the effect of temperature on the hydrolysis of rosmarinic acid (□) and on the formation of caffeic acid (•) at 30° C., 40° C., and 50° C. using 0.02 U of enzyme per mg of rosmarinic acid.

To study the influence of temperature on the reaction rate and on the stability of the products, trials were performed at pH 6.6, in phosphate buffer (50 mM), using enzyme at 0.02 U/mg of substrate and at 30° C., 40° C. and ° C. As shown in FIG. 6, no significant differences were observed when the reaction took place at 40° C. or 50° C., whereas at 30° C. the reaction rate was much slower.

Influence of Substrate Concentration

Figure 7:
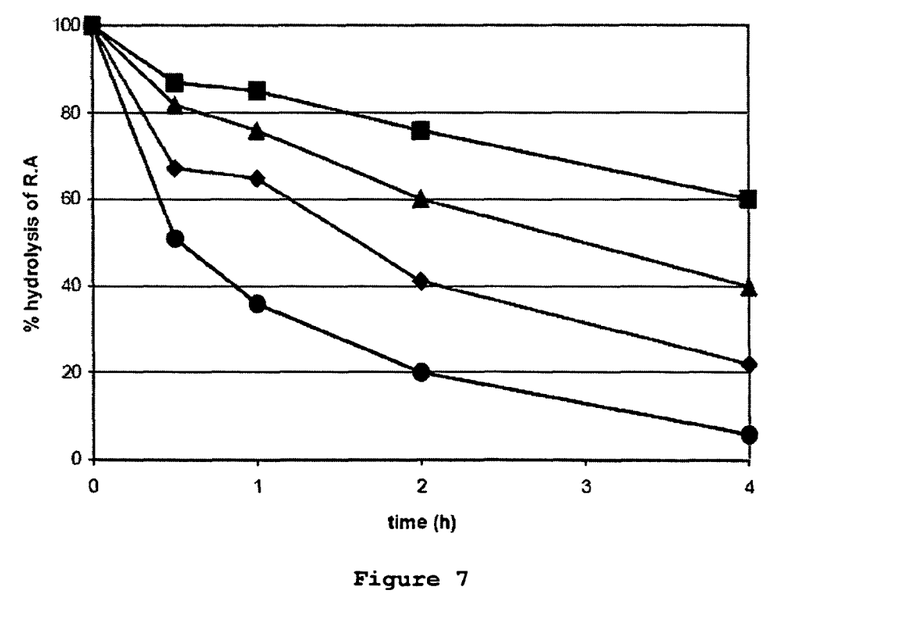
FIG. 7 is a graph showing the influence of substrate concentration on the rate of hydrolysis of rosmarinic acid and yield using (•) 1 mg, (♦) 2 mg, (▲) 4 mg, and (□) 6 mg of rosmarinic acid and 0.02 units of enzyme at pH 6.6 and 40° C.

The influence of substrate concentration on the reaction rate and yield was investigated at 40° C., pH 6.6 using 0.02 units of enzyme and 1 mg, 2 mg, 4 mg, or 6 mg of rosmarinic acid. FIG. 7 shows that the reaction rate and yield were strongly influenced by the ratio enzyme/substrate.

Indeed, more than 90% of rosmarinic acid was hydrolysed after 4 h when 1 mg of substrate was used while only 40% hydrolysis was observed when 6 mg of substrate were used under the same conditions.

Example 4

Cleavage of Rosmarinic Acid with Microorganisms

1. Incubation with *Lactobacillus johnsonii* (CNCM I-1225)

The bacterium was grown in MRS medium for 16 hours at 37° C. under anaerobic conditions. After centrifugation, the cell pellets were washed 3 times with 10 ml of sodium phosphate buffer (50 mM, pH 8). The cells (0.60 g) were suspended in 1 ml sodium phosphate buffer (50 mM, pH 8) and rosmarinic acid was added (5 mg/mL) and the mixture was incubated at 45° C. during 24 h. An aliquot was withdrawn every % hour for kinetic study. After centrifugation, the supernatants were analysed by HPLC. After 4 h incubation, all rosmarinic acid was transformed into caffeic acid and 3,4-dihydroxy phenyllacetic acid.

2. Incubation with *Bifidobacterium lactis* (CNCM I-3446)

The bacterium was grown in MRS+0.05% cystein medium for hours at 37° C. under anaerobic conditions. After centrifugation, the cell pellets were washed 3 times with 10 ml of sodium phosphate buffer (50 mM, pH 8). The cells (0.60 g) were suspended in 1 ml sodium phosphate buffer (50 mM, pH 8) and rosmarinic acid was added (5 mg/mL) and the mixture was incubated at 45° C. during 24 h. An aliquot was withdrawn every ½ hour for kinetic study. After centrifugation, the supernatants were analysed by HPLC. After 24 h incubation, more than 50% of rosmarinic acid was transformed into caffeic acid and 3,4-dihydroxy phenyllacetic acid.

Example 5

Test Conditions, MMP-1 (Matrix Metalloproteinase) Dosage (ELISA)

Treatment and Irradiation

The fibroblast cells were placed in a cultivating medium in 96-well plates. After pre-cultivating for 24 h, the medium was replaced with a medium containing the product to be tested (or no product for the reference). Each experimental condition was carried out in triplicate (using 3 cultivating wells).

After cultivating for 24 hours in presence (or absence) of product to be tested, the cultivating medium was removed and replaced by a buffer solution (EBSS) and the cells were kept away from any light source.

At the end of the incubation, the EBSS solution was replaced by a medium containing the compound to be tested and the plates were placed at 37° C., 5% $CO_2$.

After a 48 h treatment, the culture supernatant was collected for ELISA MMP-1 dosage. The cell viability was then evaluated on a cell layer by measuring the reduction of MTT by dehydrogenases of viable cells according to standard procedure.

Quantification of Collagenase (MMP-1)

The MMP-1 dosage (human interstitial collagenase) was realised by ELISA using a "BIOTRACK human MMP-1, ELISA system, Amersham RPN2610" kit, according to the instructions of the provider.

Data Processing

The counting data was transferred and processed with the PRISM software (Graph Pad Software). The inter-group comparisons were carried out by analysis of variance (ANOVA) using Dunnett's multiple comparison test.

The table below shows the constitutive MMP-1 release by fibroblasts. * shows significant differences with respect to the reference (p<0.01). Naturex is a commercially available natural extract comprising rosmarinic acid.

The hydrolysed Naturex is obtained by treating the natural extract comprising rosmarinic acid with a probiotic strain of Lactobacillus johnsonii (CNCM I-1225). Rosmarinic acid was at least partially transformed into caffeic acid and 3,4-dihydroxy phenyllacetic acid during the incubation.

|  |  | % reference |
|---|---|---|
| Reference 1 |  | 100 |
| Naturex PE 20 Control | 0.01 mg/ml | 99 |
| N PE20 C | 0.001 mg/ml | 93 |
| Naturex PE 20 Hydrolyzed | 0.01 mg/ml | 54* |
| N PE20 H | 0.001 mg/ml | 73 |

The results shown in the table above evidence the skin benefits provided by at least partially hydrolysed rosmarinic acid compared to non-hydrolysed rosmarinic acid. More particularly, it shows the inhibitory effect of the compositions of the invention on the expression of MMP-1.

The invention claimed is:

1. A topical composition comprising rosmarinic acid in combination with hydrolysis effective amounts of a probiotic microorganism containing or producing a hydrolytic enzyme of an esterase so that the rosmarinic acid is hydrolyzed to provide caffeic acid and 3,4-dihydroxy phenyllactic acid in the composition in amounts sufficient to provide an inhibitory effect on the expression of matrix metalloproteinase-1 compared to non-hydrolysed rosmarinic acid containing compositions when the composition is applied to skin; wherein the composition is in the form of an aqueous, aqueous-alcoholic or oily solution, a dispersion of the solution, lotion, or serum type, an emulsion that has a liquid or semi-liquid consistency, obtained by dispersion of a fatty phase in an aqueous phase (O/W) or vice-versa (W/O), or a suspension or emulsion that has a soft, semi-solid or solid consistency, microcapsules, microparticles or vesicular dispersions, wherein the topical composition is useful for treating skin damage.

2. The composition according to claim 1, wherein the probiotic microorganism is selected from the group consisting of bacteria, yeasts and fungi.

3. The composition according to claim 2, wherein the probiotic microorganism is selected from the group consisting of Lactobacillus johnsonii (CNCM I-1225), Bifidobacterium longum (ATCC BAA-999), Bifidobacterium lactis (CNCM I-3446) and mixtures thereof.

4. The composition according to claim 1, which further comprises ingredients selected from the group consisting of carbohydrates, proteins, lipids, vitamins, prebiotics, minerals, plant extracts, fibres, excipients, and flavourings.

5. The composition according to claim 1, wherein the probiotic microorganism is Lactobacillus johnsonii (CNCM I-1225).

* * * * *